United States Patent [19]

Bückman

[11] Patent Number: 5,399,681
[45] Date of Patent: Mar. 21, 1995

[54] METHOD FOR PREPARING $N^6$-SUBSTITUTED NAD, NADP OR FAD

[75] Inventor: Andreas F. Bückman, Brunswick, Germany

[73] Assignees: Gesellschaft fur Biotechnologische Forschung mbH (GBF), Brunswick; Degussa AG, Hanau, both of Germany

[21] Appl. No.: 469,760

[22] Filed: Jan. 24, 1990

Related U.S. Application Data

[63] Continuation of Ser. No. 52,555, May 21, 1987, abandoned.

[30] Foreign Application Priority Data

May 24, 1986 [DE] Germany ............... 36 17 535.8

[51] Int. Cl.⁶ ............................................. C07H 21/02
[52] U.S. Cl. ...................... 536/26.24; 536/26.25; 536/112; 536/123.1; 536/124; 525/54.2; 525/54.3; 525/58; 525/326.9; 525/327.4; 525/329.6; 525/403; 528/403
[58] Field of Search ............ 536/27, 28, 29, 26.24, 536/26.25, 112, 123.1, 124; 525/54.2-54.3, 58, 326, 327.4, 329.6, 403; 528/403

[56] References Cited

U.S. PATENT DOCUMENTS 4,443,594  4/1984  Buckmann .................... 536/27

OTHER PUBLICATIONS

Buckmann et al., *Adv. Biochem. Engin./Biotech.*, 69, pp. 97–152 (1989).
Schmidt et al., *Eur. J. Biochem.*, 67, 295–302 (1976).
Zappelli et al., *Eur. J. Biochem.*, 54, 475–482 (1975).
Okuda et al., *Eur. J. Biochem.*, 151, 33–38 (1985).
Muramatsu et al., *Eur. J. Biochem.*, 80, 111–117 (1977).
Zappelli et al., *Eur. J. Biochem.*, 72, 309–315 (1977).
Lindberg et al., *Eur. J. Biochem.*, 40, 187–193 (1973).
Lowe et al., *Eur. J. Biochem.*, 49, 511–520 (1974).
Kochetkov et al., Organic Chemistry of Nucleic Acids, Part B, Plenum Press, New York, N.Y., 1972, pp. 309–311; 393–396.
March, Advanced Organic Chemistry, McGraw-Hill Book Co., New York, N.Y., 1968, pp. 335–339.

*Primary Examiner*—John W. Rollins
*Assistant Examiner*—L. Eric Crane
*Attorney, Agent, or Firm*—Kane, Dalsimer, Sullivan, Kurucz, Levy, Eisele and Richard

[57] ABSTRACT

The invention relates to a method of preparing $N^6$-substituted NAD, NADP or FAD by Dimroth rearrangement, wherein the rearrangement is carried out without preceding reduction and subsequent reoxidation.

9 Claims, No Drawings

METHOD FOR PREPARING N⁶-SUBSTITUTED NAD, NADP OR FAD

CROSS-REFERENCE TO RELATED APPLICATION

This application is a continuation of my copending U.S. patent application Ser. No. 52,555, filed May 21, 1987, and now abandoned.

BACKGROUND OF THE INVENTION

1. Field of the Invention

The invention relates to a process for preparing $N^6$-substituted NAD, NADP or FAD by Dimroth rearrangement.

2. Brief Description of the Prior Art

NAD(H) or NADP(H) bound to solid polymeric supports or to water-soluble macromolecules have already been under investigation and in use for about 15 years. The coenzymes bound to solid supports are successfully used in affinity chromatography (1). Water-soluble macromolecular NAD(H) or NADP(H) is used as enyzmatically regeneratable coenzyme derivative in enzyme membrane reactors for the continuous preparation of fine chemicals by coenzyme-dependent enzymatic catalysis (2).

A conventional strategy for synthesis of these macromolecular NAD(H) or NADP(H) derivates is: alkylation of the N(1) position of the adenine ring system of NAD or NADP, chemical reduction to N(1)-alkylated NADH or NADPH, Dimroth rearrangement in the basic medium and at elevated temperatures (pH 10–11, 60°–70° C.) to $N^6$-alkylated NADH or NADPH, covalent binding of said reduced coenzyme to the macromolecule or enzymatic oxidation to the $N^6$-alkylated NAD or NADP and subsequent covalent linking to the macromolecule.

For NAD and NADP the reaction sequence has been employed in the case of the alkylation agents such as iodoacetic acid (3,4), propiolactone (5), 3,4-epoxy butyric acid (6,7) or ethyleneimine (8,9). Coenzymes alkylated in this manner have for the covalent bonding to macromolecules carboxyl or amino groups at the end of the chain at the $N^6$-atom of the adenine ring.

For the linking insoluble macromolecules (solid supports, matrices) or soluble, in particular water-soluble, macromolecules are possible Which have one or more functional groups active for the linking. The macromolecules may per se have such functional groups or the functional groups can be introduced into the macromolecules by methods known to the expert. Examples of macromolecules which can be used are: dextrans, polyethylene glycols, polyethyleneimines, polyacrylamides, copolymers such as methylvinyl ether/maleic anhydride, ethylene/maleic anhydride, divinyl ether/maleic anhydride, agarose, glass, cellulose, silica gel, and derivatives of the macromolecules. For the synthesis of macromolecular coenzyme derivatives alternative strategies have been developed which can be considered as variants of the conventional strategy and are intended in many cases to simplify the synthesis. Thus, a covalent coupling has been described which is catalyzed by transglutaminase in the case of binding the conventionally synthesized $N^6$-[(6-aminohexyl)carbamoylmethyl[-NAD⁺ to water-soluble proteins, for example casein via γ-carboxyamide groups of the L glutamine (10).

It is also possible to prepare firstly $N^6$-vinyl derivatives of NAD in conventional manner and to copolymerize them with other vinyl monomers to give macromolecular NAD (5). A simplified copolymerization method (preparation N(1)-vinyl-NAD⁺ derivative and simultaneous copolymerization and Dimroth rearrangement) gave a macromolecular NAD derivative which could only be reduced enzymatically to a limited ($<40\%$) extent (11). Based on water-soluble polymers with epoxy groups a method is known in which proceeding from unmodified NAD the N(1)-alkylation, reduction to N(1)-alkylated NADH and Dimroth rearrangement to $N^6$-alkylated NADH in covalently bound state at the polymer was carried out in a three-step method (12). Proceeding from NADH even a one-step method is possible because coupling by N(1)-alkylation and Dimroth rearrangement in the basic medium can take place simultaneously under the same conditions. In the best macromolecular NADH was obtained which was oxidizable enzymatically to about 60%.

These simplified methods have the disadvantage that not very well defined macromolecular NAD(H) derivatives arise due to secondary reactions at the coenzyme which are the main cause of the limited oxidizability or reducibility.

SUMMARY OF THE INVENTION

A compromise between the simplified and conventional methods with the advantage of uniformity of the coupled NADH-analogue was achieved with the following method: synthesis of the N(1)-(2-aminoethyl)-NAD, covalent binding to a water-soluble polymer to give macromolecular N(1)-(2-aminoethyl)-NAD, chemical reduction to macromolecular N(1)-(2-aminoethyl)-NADH and Dimroth rearrangement to macromolecular $N^6$-(2-aminoethyl)-NADH (13,14).

It is emphasized that all the methods for preparing macromolecular NAD(H) or NADP(H) with well defined coenzymes have in common the step of Dimroth rearrangement of reduced N(1)-alkylated coenzyme. This rearrangement takes place under extreme conditions for the coenzyme and as a result considerable losses can occur in the uncoupled state (pH 10.5–11.2, temp. 60°–70° C., time 1.5–2 h).

For N(1)-(carboxymethyl)-ATP the conditions of the Dimroth rearrangement to $N^6$-(carboxymethyl)-ATP could be improved by adding an anion exchanger in OH⁻ form to the aqueous N(1)-(carboxymethyl)-ATP solution for presumed stabilization of the triphosphate group (15). By HPLC it was possible to detect the complete Dimroth rearrangement with greatly reduced product decomposition within 5, 10 or 240 minutes during the incubation at 100°, 75° or 50° C. respectively. Proceeding from N(1)-(carboxymethyl)-NAD it was not possible in an equivalent operation to produce any coenzymatically active $N^6$-(carboxymethyl)-NAD (15).

DETAILED DESCRIPTION OF THE PREFERRED EMBODIMENTS OF THE INVENTION

According to one embodiment the invention relates to a method for preparing NAD or NADP bound to macromolecules wherein the adenine ring system of the coenzyme is alkylated in 1-position with ethyleneimine to N(1)-(2-aminoethyl)-NAD or N(1)-(2-aminoethyl)-NADP, the coenzyme alkylated in this manner rearranged in the oxidized state in aqueous medium to $N^6$-(2-aminoethyl)-NAD or $N^6$-(2-aminoethyl)-NADP under conditions extremely mild for the Dimroth rearrangement (preferably pH 5–8, temp 50° C. time 6–8 h), and $N^6$-(2-aminoethyl)-NAD or $N^6$-(2-aminoethyl)-NADP subsequently bound to polymers with groups reactive for primary amino groups.

FAD derivates, synthesized by modification of the $N^6$-position of the adenine ring, have hitherto been described in two cases in conjunction with the immobilization on water-soluble polymers or solid supports. Zapelli et al. (16) coupled $N^6$-(2-hydroxy-3-carboxypropyl)-FAD to polyethyleneimine, synthesized by Dimroth rearrangement under extreme conditions (pH 10, 80° C.) of the N(1)-(2-hydroxy-3-carboxypropyl)-FAD after alkylation of the FAD with 3,4-epoxybutyric acid. They showed that for D-amino acid oxidase and glucose oxidase having non-covalently bound and thus bleedable FAD the longtime stability in the immobilized form could be greatly improved in the presence of the polyethyleneimine-$N^6$-(2-hydroxy-carboxypropyl)-FAD, acting as continuous FAD supply.

Narasimhan and Wingard (17) immobilized on indium/tin oxide electrodes FAD which react with formaldehyde-activated aminosilane groups present, thereby giving directly a —NH—$CH_2$—NH bond via the $N^6$-position of the adenine ring. There were thereby able to reduce the overpotential of NADH by 180 mV although this was not enough to oxidize NADH to NAD satisfactorily at the electrode. The authors mention the probability that by secondary reactions other coupling positions at the FAD molecule could also be involved in the immobilization.

$N^6$-amino-alkylated FAD derivates, e.g. $N^6$-(2-aminoethyl)-FAD, have so far not been described. The described conversion according to the invention of N(1)-(aminoethyl)-adenine to $N^6$-(2-aminoethyl)-adenine derivates of NAD and NADP under unexpectedly mild conditions in an aqueous medium can be carried out according to a further embodiment of the invention also for N(1)-(aminoethyl)-FAD with $N^6$-(2-aminoethyl)-FAD with similar conversion percentages as in the transformation of the N(1)-(2-aminoethyl)-NAD.

Preparation of macromolecular NAD

A. Preparation of N(1)-(2-aminoethyl)-NAD 200 g (300 mmol) NAD (oriental yeast, free acid) were dissolved in 400 ml distilled water. Slowly added thereto were 42.5 ml (850 mmol) ethyleneimine (Serva), keeping the pH value at 3.2+0.05 with 70%.perchloric acid (total volume 650 ml). The reaction mixture was stirred for 50 h at 30° C. and pH 3.2+0.05 (set with 70% perchloric acid). The conversion of the NAD to N(1)-(2-aminoethyl)-NAD was determined by UV scanning with thin-film chromatography on silica gel (DC alu foils silica gel 60 $F_{254}$, film thickness 0.2 mm, E. Merck) with mobile phase isobutyric acid/distilled water/25% $NH_3$ in water 66/33/1 (vol./vol./vol.), pH 3.7. The reaction mixture was made up with the distilled water to 1 liter. By precipitation repeated 5 times and subsequent centrifuging with in each case 10 times the amount of industrial ethanol at 4° C. the ethyleneimine not reacted and soluble in ethanol as removed. The precipitate was dried in vacuo at 25° C. in a drying oven and kept in a desiccator over NaOH at 4° C. For the fractionation 20 g of the dried reaction mixture of the composition 5.3 mmol NAD (23%), 15 mmol N(1)-(2-aminoethyl)-NAD (65%) and 2.6 mmol byproducts (12%) in distilled water up to 40 ml. After setting the pH to 5.0 with 10N NaOH the solution was introduced at 4° C. to a cation exchange column (100×2.6 cm, Biorex 70, 50–100 meshes, Bio-Rad) which had been brought into equilibrium against 0.01M LiCl, pH 4.5. After the charging the NAD was eluted in a 2 liter fraction quantitatively with 0.01M LiCl, pH 4.5 (5.3 mmol). Further elution with 2 l 0.01M LiCl, pH 4.5, gave 2.5 mmol of a mixture having two compounds which behaved in thin-film chromatography like $N^6$-(2-aminoethyl)-NAD and the presumed 1, $N^6$-ethanadenine-NAD which as described under B can easily form from N(1)-(2-aminoethyl)-NAD.

The column was now shortened to 50 cm length by lowering the column filling to achieve a more rapid elution of the main product N(1)-(2-aminoethyl)-NAD. This elution was carried out with 1.5 l 0.2M LiCl, pH 4.7, and 11.3 mmol pure N(1)-(2-aminoethyl)-NAD recovered. Byproducts (2.6 mmol) arising during the alkylization by ethyleneimine were not isolated.

The various fractions were concentrated under reduced pressure (flash evaporation) to 30 ml and precipitated 5 times with industrial ethanol (20 times excess by volume), thereby separating the LiCl which is readily soluble in ethanol. The products of the fractions were freeze dried after dissolving in as little distilled water as possible and stored at 4° C. in a desiccator over NaOH.

The fractionation obtained is summarized in the following table:

| Compound | mmol in the reaction mixture | mmol after fractionation | % recovery | % of mmol introduced to column |
| --- | --- | --- | --- | --- |
| NAD | 5.3 | 5.3 | 100 | 23 |
| N(1)-(2-aminoethyl)-NAD | 15 | 11.3 | 75 | 49 |
| Byproducts formed during alkylation | 2.6 | — | — | — |
| Byproducts formed on Biorex 70 column from N(1)-(2-aminoethyl)-NAD | — | 2.5 | 16.6*) | 11 |

*) % related to N(1)-(2-aminoethyl)-NAD in the reaction mixture

N(1)-(2-aminoethyl)-NAD gives a positive reaction with ninhydrin (primary amino groups are present) and exhibits a shoulder in the region of 300–310 nm at pH 11.5 characteristic of N(1)-alkylation in the adenine ringe.

B. Preparation and purification of $N^6$-(2-aminoethyl)-NAD 2 g (2.78 mmol) N(1)-(2-aminoethyl)-NAD was dissolved in 200 ml distilled water and set to pH 6.5 with 1N LiOH. This solution was incubated in a water bath at 50° C. for 7 hours. Each hour the pH value was set with 1N LiOH. After thin-film chromatography according to A it was detected that two compounds had arisen from N(1)-(2-aminoethyl)-NAD, that is $N^6$-(2-aminoethyl)-NAD (rf=0.13) and the presumable 1,$N^6$-ethanadenine-NAD (rf=0.068). The composition of the incubation solution was determined by UV scanning by thin-film chromatography: 62.5% (1.74 mmol) $N^6$-(2-aminoethyl)-NAD and 37.5% (1.04 mmol) 1,$N^6$-ethanadenine-NAD.

The freeze-dried reaction mixture was dissolved in 16.5 ml distilled water and set to pH 5.5 with 1N LiOH. This solution was introduced into a cation exchanger column (100×1.6 cm, Biorex 70, 50–100 meshes, Bio- Rad) which had been brought into equilibrium against 0.01M LiCl, pH 3.5. By elution at 4° C. with 0.01M LiCl, pH 3.5, the two compounds were separately eluted with slight overlapping, $N^6$-(2-aminoethyl)-NAD leaving the column last.

Three thin-film-chromatographically uniform fractions with 1,$N^6$-ethanadenine-NAD (0.98 mmol in 250 ml), mixture (0.20 mmol in 120 ml) and pure $N^6$-(2-aminoethyl)-NAD (1.56 mmol in 660 ml) were concentrated under reduced pressure to 3 ml and precipitated for removal of LiCl twice with cold industrial ethanol (20 times excess by volume). After dissolving in as little distilled water as possible the fractions were freeze dried and stored at 4° C. in a desiccator over NaOH. The purification obtained is summarized in the following table.

| Compound | mmol in incubation solution | mmol after fractionation | % recovery | % of mmol introduced into column |
|---|---|---|---|---|
| 1,$N^6$-(ethanadenine)-NAD | 1.04 | 0.98 | 94.2 | 30.8 |
| Mixture | — | 0.21 | — | 7.7 |
| $N^6$-(2-aminoethyl)-NAD | 1.73 | 1.56 | 90 | 56.5 |

UV spectra and NMR data have confirmed $N^6$-(2-aminoethyl)-NAD as such. The compound gives a positive reaction with ninhydrin (primary amino group present). $\lambda_{max}$ lies at 267 nm and the compound no longer exhibits a shoulder in the range 300–310 nm at pH 11.5, which would be characteristic for N(1)-alkylation of the adenine ring. Quantitative reduction, catalyzed by beer yeast alcohol dehydrogenase, gives fluorescent $N^6$-(2-aminoethyl)-NADH (excitation at 366 nm) with extinction at 267 nm/extinction at 338 nm = 3.2, characteristic of $N^6$-alkylated NADH derivatives.

C. Example 1: Preparation of polyethylene glycol $N^6$-(2-aminoethyl)-NAD 2 g carboxylated polyethylene glycol (M 20000, 0.1 mmol with 0.14 mmol carboxyl groups), made according to Bueckmann et al. (Makromol. Chem. 182, 1379–1384/1981/),were dissolved in distilled water up to 4 ml and 2 ml with 125 μmol $N^6$-(2-aminoethyl)-NAD added. After pH setting to 4.7 with 1N HCl, 200 mg (1.04 mmol) 1-(3-dimethylaminopropyl)-3-ethyl-carbodiimide-HCl were added within 10 minutes in two equal portions. The reaction mixture was stirred for 2 hours at room temperature (pH setting in the range 4.5–4.8 with 1N HCl or 1N NaOH). After incubation for 16 hours at 4° C. the reaction mixture (7 ml) was gel-filtered in two batches of 3.5 ml through a Sephadex G 50 column (100×2.6 cm) in equilibrium against distilled water. The combined fractions with polyethylene glycol-$N^6$-(2-aminoethyl)-NAD were concentrated under reduced pressure to 15 ml with 85 μmol $N^6$-(2-aminoethyl)-NAD (concentration 5.5 mM) bound to polyethylene glycol with coupling yield of 68%.

D. Example 2: Preparation of dextran-$N^6$-(2-aminoethyl)-NAD 0.2 g carboxylated dextran T 70 (M 70000, 1 mmol anhydroglucose monomers, of which 0.3 mmol were carboxylated), made according to Bueckmann et al., J. Appl. Biochem. 3, 301–315 (1981), were dissolved in 2 ml distilled water and 1 ml with 65 μmol $N^6$-(2-aminoethyl)-NAD added. After setting the pH to 4.7 with 1N HCl, 150 mg (0.78 mmol) 1-(3-dimethylaminopropyl)-3-ethyl-carbodiimide-HCl were added within 10 minutes in two equal portions. The reaction mixture was stirred for 2 hours at room temperature (pH setting in the range 4.5–4.8 with 1N HCl or 1N NaOH). After incubation at 4° C. for 16 hours the reaction mixture (3.5 ml) was gel filtered at 4° C. through a Sephadex G50 ; column (100×2.6 cm) in equilibrium against distilled water. The fraction with dextran-$N^6$-(2-aminoethyl)-NAD was concentrated under reduced pressure to 10 ml with 14 μmol $N^6$-(2-aminoethyl)-NAD (concentration 1.4 mM) bound to dextran with a coupling yield of 22%.

E. Example 3: Preparation of polyvinylpyrrolidone $N^6$-(2-aminoethyl)-NAD 0.3 g carboxylated polyvinylpyrrolidone (M 160000, 2.7 mmol vinylpyrrolidone monomer with 0.135 mmol carboxly groups), made according to Specht, Hoppe-Seyler's journal Physiol. Chem. 354, 1659–1660 (1973), were dissolved in 3 ml distilled water, 100 mg (63 μmol) $N^6$-(2-aminoethyl)-NAD added and the pH value set to 4.7 with 1N HCl. 150 mg (0.78 mmol) 1-3-diemethylaminopropyl)-3-ethyl-carbodiimide-HCl were added within 10 minutes in two equal proportions. The reaction mixture was stirred for 2 hours at room temperature (pH setting in the range 4.5–4.8 with 1N HCl or 1N NaOH). After incubation at 4° C. for 16 hours the reaction mixture (3.8 ml) was gel filtered at 4° C. through a Sephadex G 50 column (100×2.6 cm) in equilibrium against distilled water. The fraction with polyvinylpyrrolidone-$N^6$-(2-aminoethyl)-NAD was concentrated under reduced pressure to 10 ml with 10 μmol $N^6$-(2-aminoethyl)-NAD (concentration 1 mM) bound to polyvinylpyrrolidone with a coupling yield of 16%.

F. Example 4: Preparation of poly-(ethylene/maleic acid)-$N^6$-(2-aminoethyl)-NAD 50 mg poly-(ethylene/maleic anhydride) (M unknown, 0.4 mmol ethylene/maleic anhydride monomer, Aldrich) were dissolved in 10 ml distilled water (pH setting) to 7.5 with 1N NaOH) and 20 μmol $N^6$-(2-aminoethyl)-NAD added. After 5 hours stirring at room temperature (pH setting to 7.5 with 1N NaOH) the reaction mixture was dialyzed against 5 l distilled water at 4° C. for 16 hours. 22 ml with 13 μmol $N^6$-(2-aminoethyl)-NAD (concentration 0.6 mM) bound to poly-(ethylene/maleic acid) with a coupling yield of 65% were obtained.

G. Example 5: Preparation of poly-(methylvinyl ether/maleic acid)-$N^6$-(2-aminoethyl)-NAD 50 g poly-(methylvinyl ether/maleic anhydride) (M 20000, 0.32 mmol methylvinyl ether/maleic anhydride monomer, polysciences) were dissolved in 10 ml distilled water (pH setting to 7.5 with 1N NaOH) and 20 μmol $N^6$-(2-aminoethyl)-NAD added. After 5 hours stirring at room temperature (pH setting to 7.5 with 1N NaOH) the reaction mixture was dialyzed against 5 l distilled water at 4° C. for 16 hours. 22 ml with 17 μmol $N^6$-(2-aminoethyl)-NAD (concentration 0.78 mM) bound to poly(methylvinyl ether/maleic acid) were obtained with a coupling yield of 85%.

H. Example 6: Preparation of poly-(divinyl ether/maleic acid)-$N^6$-(2-aminoethyl)-NAD 50 mg poly-(divinyl ether/maleic anhydride) (M 18000, 0.16 mmol divinyl ether/maleic anhydride momoner, Hercules) were dissolved in 10 ml distilled water (pH-setting to 7.5 with 1N NaOH) and 20 μmol $N^6$-(2-aminoethyl)-NAD added. After 5 hours stirring at room temperature (pH setting to 7.5 with 1N NaOH) the reaction mixture was dialyzed against 5 l distilled water at 4° C. for 16 hours. 22 with 20 μmol $N^6$-(2- aminoethyl)-NAD (concentration 0.92 mM) bound to poly-(divinyl ether/maleic acid) was obtained with a coupling yield of 100%.

The enzymatic reducibility of the water-soluble polymer-bound $N^6$-(2-aminoethyl)-NAD derivatives was determined compared with $N^6$-(2-aminoethyl)-NAD with the reaction catalyzed by yeast alcohol dehydrogenase under the following conditions:

0.1M tris/HCl, pH 8.2, room temperature
0.1M ethanol
7 mM semicarbazide/HCl
0.1 mM $N^6$-(2-aminoethyl)-NAD
free or polymer-bound)
0.3 mg alcohol dehydrogenase The reducibility data are summarized in the following table:

|  | Reducibility % |
| --- | --- |
| $N^6$-(2-aminoethyl)-NAD | 100 |
| Polyethylene glycol (M 20000)-$N^6$-(2-aminoethyl)-NAD | 90 |
| Dextran T 70 (M 70000)-$N^6$-(2-aminoethyl)-NAD | 90 |
| Polyvinylpyrrolidone (M 160000)-$N^6$-(2-aminoethyl)-NAD | 90 |
| Poly-(ethylene/maleic acid)-$N^6$-(2-aminoethyl)-NAD | 60 |
| Poly-(methylvinyl ether/maleic acid)-$N^6$-(2-aminoethyl)-NAD | 70 |
| Poly-(divinyl ether/maleic acid)-$N^6$-(2-aminoethyl)-NAD | 60 |

Note: For $N^6$-(2-aminoethyl)-NAD and $N^6$-(2-aminoethyl)-NADH derivatives $\epsilon_{267}=21000$ $M^{-1}$ $cm^{-1}$ and $\epsilon_{340}=6220$ $M^{-1}cm^{-1}$ as extiction coefficients.

I. Example 7: Preparation of CH-sepharose 4B-$N^6$-(2-aminoethyl)-NAD 1.5 g CH-sepharose 4B (Pharmacia, with 60–84 μmol carboxyhexyl groups) steeped in 10 ml distilled water were washed over a glass frit with 100 ml distilled water. The half-dried CH-sapharose 4B was suspended in 2 ml distilled water and 430 mg (2.25 mmol) 1-(3-dimethylaminopropyl)-3-ethyl carbodiimide-HCl added. The suspension was incubated for 10 min at room temperature (pH setting to 4.8–5.0 with 1N NaOH or 1N HCl). The activated CH-sepharose 4B was washed twice within 1 minute with 25 ml distilled water and added to 2 ml aqueous solution with 34 μmol $N^6$-(2-aminoethyl)-NAD. The suspension was incubated for 16 hours at room temperature after pH setting to 4.6 (1N NaOH or 1N HCl).

After washing with 75 ml 20% LiCl and 25 ml distilled water and sedimentation in distilled water 7 ml CH-sepharose 4B-$N^6$-(2-aminoethyl)-NAD with 20.6 μmol bound $N^6$-(2-aminoethyl)-NAD NAD (concentration 3 mM) were obtained with a coupling yield of 60.5%.

Preparation of macromolecular NADP

A. Preparation and purification of N(1)-(2-aminoethyl)-NADP 7.5 g (9.51 mmol) NADP (Boehringer, di-sodium salt) were dissolved in 10 ml distilled water. To this 1.4 ml (28 mmol) ethyleneimine (Serva) were slowly added, the pH value being kept at 3.35±0.05 with 70% perchloric acid (total volume 25 ml). The reaction mixture was stirred for 120 hours at 30° C., pH 3.35±0.05 (set with 70% perchloric acid). The conversion of the NADP to N(1)-(2-aminoethyl)-NADP was determined by UV scanning by thin-film chromatography on silica gel (DC-alu foils-silica gel 60 $F_{254}$, film thickness 0.2 mm, E. Merck) with mobile phase isobutyric acid/distilled water/25% $NH_3$ in water=66/33/1 (vol./vol./vol.), pH 3.7. The reaction mixture was brought with distilled water to 50 ml. By repeating precipitation 5 times and subsequent centrifuging with in each case 10 times the amount industrial ethanol at 4° C. the unconverted ethyleneimine soluble in ethanol was removed. The precipitate was dissolved in as little distilled water as possible and freeze dried. The lyophilisate was kept in a desiccator over NaOH at 4° C.

For the fractionation 0.75 g freeze-dried reaction mixture with the composition 0.235 mmol NADP (27.5%), 0.575 mmol N(1)-(2-aminoethyl)-NADP (68%) and 0.038 mmol byproducts (4.5%) were dissolved in distilled water up to 22 ml. After pH setting to 3.5 with 1N HCl this solution was introduced into a cation exchanger-column (60×1.5 cm, AG W50 $X_4$, 100–200 meshes, Bio-Rad) which had been brought into equilibrium against 0.01M triethanolamine bicarbonate, pH 3.5. By elution at 4° C. with 0.01M triethanolamine bicarbonate, pH 3.5, three fractions were successively obtained: NADP (0.29 mmol, 34% in 25 ml) contamined with byproducts, byproducts (0.115 mmol, 13.5% in 100 ml), formed during the alkylation reaction from N(1)-(2-aminoethyl)-NADP and during the fractionation in the column, and pure N(1)2-aminoethyl)-NADP (0.39 mmol, 46%, in 200 ml).

The fractions were concentrated under reduced pressure up to 25 ml and freeze dried to remove the triethanolamine bicarbonate and stored at 4° C. in a desiccator over NaOH. The fractionation achieved is summarized in the following table.

| Compound | mmol in reaction mixture | mmol after fractionation | % recovery | % mmol introduced into column |
| --- | --- | --- | --- | --- |
| NADP | 0.235 | 0.235 | 100 | 27.5 |
| Byproducts | 0.038 | 0.17 | — | 20 |
| N(1)-(2-aminoethyl)-NADP | 0.575 | 0.39 | 68 | 49 |

N(1)-(2-aminoethyl)-NADP gives a positive reaction with ninhydrin (primary amino groups are present) and exhibits a shoulder in the range 300–310 nm at pH 11.5 characteristic of N(1)-alkylation in the adenine ring.

B. Preparation and purification of $N^6$-(2-aminoethyl)-NADP 0.35 g (0.24 mmol) N(1)2-aminoethyl)-NADP were dissolved in 0.5 l distilled water and set with 1N LiOH to a pH value of 6.0. This solution was incubated in a water bath at 50° C. for 4 hours. A pH setting was made every hour with 1N LiOH. By thin-film chromatography according to A it was detected that two compounds of N(1)-(2-aminoethyl)-NADP had formed, i.e. $N^6$-(2-aminoethyl)-NADP (rf=0.048) and the presumed 1,$N^6$-ethane-adenine-NADP (rf=0.031). The composition of the incubation solution was determined by UV scanning at 260 nm by thin-film chromatography: 75% 1,$N^6$-ethane-adenine-NADP (0.18 mmol) and 25% $N^6$-(2-aminoethyl)-NADP (0.06 mmol).

The incubation solution was concentrated under reduced pressure to 7 ml. After pH setting to 5.0 this solution was introduced at 4° C. to an anion exchanger column (100×1.6 cm, $AG_1X_4$, 100–200 meshes, Bio-Rad) which had been brought into equilibrium against 0.01M triethanolamine bicarbonate, pH 3.5. By elution with 0.01M triethanolamine bicarbonate, pH 3.5, elution was carried out successively into two main fractions: 1,$N^6$-ethane-adenine-NADP (0.17 mmol, 70% in 1 liter) and $N^6$-(2-aminoethyl)-NADP (0.053 mmol, 22%, in 250 ml).

The two fractions were concentrated under reduced pressure to 2 ml and to remove the triethanolamine bicarbonate eluted twice at room temperature through a Sephadex G10 column (100×1.5 cm) which had been brought into equilibrium against distilled water.

After freeze drying both products were stored in a desiccator over NaOH at 4° C. The fractionation obtained is summarized in the following table:

| Compound | mmol in incubation solution | mmol after fractionation | % recovery | % of mmol into column |
|---|---|---|---|---|
| 1,$N^6$-ethane-adenine-NADP | 0.18 | 0.17 | 94.4 | 70.8 |
| $N^6$-(2-aminoethyl)-NADP | 0.06 | 0.053 | 88.3 | 22.0 |

UV spectra and NMR data have confirmed $N^6$-(2-aminoethyl)-NADP as such. The compound gives a positive reaction with ninhydrin (primary amino group present), has $\lambda_{max}$ at 267 nm and no longer exhibits any shoulder in the range 300–310 nm at pH 11.5, which would be characteristic of N(1)-alkylation of the adenine ring. Quantitative reduction, catalyzed by beer yeast glucose-6-phosphate dehydrogenase, gives fluorescent $N^6$-(2-aminoethyl)-NADPH (excitation at 366 nm) with extinction at 267 nm/extinction at 338=3.2, characteristic of $N^6$-alkylated NADPH derivates.

C. Example 1: Preparation of polyethylene glycol $N^6$-(2-aminoethyl)-NADP

PEG ($M_r$=4000)-$N^6$-(2-aminoethyl)-NADP:

60 mg N-hydroxysuccinimide-activated, carboxylated polyethylene glycol (M 4000, 0.015 mmol with 0.03 mmol activated carboxyl groups), made according to Bueckmann et al., Makromol. Chem. 182, 1379–1384 (1981), was dissolved in 1 ml distilled water with 15 mmol $N^6$-(2-aminoethyl)-NADP, at pH 7.2, set with 1N NaOH. The mixture was stirred for 5 hours at room temperature and pH 7.2, (pH setting with 1N NaOH). The reaction mixture was gel-filtered at 4° C. through a Sephadex G50 column (100×2.6 cm) in equilibrium against distilled water. The fraction with polyethylene glycol-$N^6$-(2-aminoethyl-NADP was concentrated to 10 ml with 12 μmol $N^6$-(2-aminoethyl)-NADP (concentration 1.2 mM) bound to polyethylene gylcol ($M_r$4000) with a coupling yield of 80%.

PEG ($M_r$=20000)-$N^6$-(2-aminoethyl)-NADP:

325 mg N-hydroxysuccinimide-activated carboxylated polyethylene glycol ($M_r$=20000, 0.015 mmol with 0.03 mmol activated carboxyl groups), prepared according to Bueckmann et al., Makromol. Chem. 182, 1379–1384 (1981), were dissolved in 1 ml distilled water with 15 μmol $N^6$-(2-aminoethyl)-NADP at pH 7.2, set with 1N NaOH. Stirring was carried out for 1 hour at room temperature at pH 7.2–7.3 and 3 hours at pH 6.8 (1N HCl or 1N NaOH). The reaction mixture was gel-filtered at 4° C. through a Sephadex G 50 column (2.6×100 cm) in equilibrium against distilled water. The fraction with polyethylene glycol $N^6$-(2-aminoethyl)-NADP was concentrated to 10 ml with 15 μmol $N^6$-(2-aminoethyl)-NADP (concentration 1.5 mM) bound to polyethylene glycol ($M_r$=20000) with a coupling yield of 100%.

Note: The coupling method, based on activation of the carboxyl groups with 1-(3-dimethylaminopropyl)-3-ethylcarbodiimide is not possible for NADP derivatives because this reagent also effects the 2.3 cyclization via the 2-phosphate group of the ribose at the adenine side of the molecule, NADP derivatives thereby losing the coenzyme activity.

D. Example 2: Preparation of poly-(ethylene/maleic acid)-$N^6$-(2-aminoethyl)-NADP 12 mg poly-(ethylene/maleic anhydride) (M unknown, 0.1 mmol ethylene/maleic anhydride monomer, Aldrich) were dissolved in 1 ml distilled water (pH setting to 7.5 with 0.2N NaOH) and 5.5 μmol $N^6$-(2-aminoethyl)-NADp added. After 5 hours stirring at room temperature (pH setting to 7.5 with 0.2N NaOH) the reaction mixture was dialyzed against 5 liters at 4° C. for 16 hours. 3.3 ml with 0.8 μmol $N^6$-(2-aminoethyl)-NADP (concentration 0.24 mM) bound to poly-(ethylene/maleic acid) were obtained with a coupling yield of 15%.

E. Example 3: Preparation of poly-(methylvinyl ether/maleic acid)-$N^6$-(2-aminoethyl)-NADP 12 mg poly-(methylvinyl ether/maleic anhydride) (M 20000, 0.077 mmol methylvinyl ether/maleic anhydride monomer, polysciences) were dissolved in 1 ml distilled water (pH setting to 7.5 with 0.2N NaOH) and 5.5 μmol $N^6$-(2-aminoethyl)-NADP added. After 5 hours stirring at room temperature (pH setting to 7.5 with 0.2N NaOH) the reaction mixture was dialyzed against 5 litres at 4° C. for 16 hours. 4.4 ml with 0.6 μmol $N^6$-(2-aminoethyl)-NADP (concentration 0.2 mM) bound to poly-(methylyvinyl ether/maleic acid) were obtained with a coupling yield of 11%.

F. Example 4: Preparation of poly-(divinyl ether/maleic acid)-$N^6$-(2-aminoethyl)-NADP 12 mg poly-(divinyl ether/maleic anhydride) (M 18000, 0.046 μmol divinyl ether/maleic anhydride monomer, Hercules) were dissolved in 1 ml distilled water (pH setting to 7.5 with 0.2N NaOH) and 5.5 μmol $N^6$-(2-aminoethyl)-NADP added. After 5 hours stirring at room temperature (pH setting to 7.5 with 0.2N NaOH) the reaction mixture was dialyzed against 5 litres at 4° C. for 16 hours. 3.5 ml with 0.7 μmol $N^6$-(2-aminoethyl)-NADP (concentration 0.136 mM) bound to poly-(divinyl ether/maleic acid) were obtained with a coupling yield of 13%.

Note: The $N^6$-(2-aminoethyl)-NADP coupling yield for D, E and F is substantially lower compared with similar couplings in the case of $N^6$-(2-aminoethyl)-NAD. The negatively charged carboxyl groups arising from the acid anhydride will make the coupling difficult for the likewise negative $N^6$-(2-aminoethyl)-NADP molecules compared with the positively charged $N^6$-(2-aminoethyl)-NAD molecules.

The enzymatic reducibility of the water-soluble polymer-bound $N^6$-(2-aminoethyl)-NADP derivatives was determined compared with $N^6$-(2-aminoethyl)-NADP with the reaction catalyzed by yeast glucose 6-phosphate dehydrogenase under the following conditions:

0.05M triethanolamine/HCl, pH 8.0, room temperature 5.5 mM $MgCl_2$ 4.5 mM glucose-6-phosphate 0.1 mM $N^6$-(2-aminoethyl)-NADP (free or polymer-bound)

30 μg glucose-6-phosphate dehydrogenase

The reducibility data are summarized in the following table:

|  | Reducibility % |
|---|---|
| $N^6$-(2-aminoethyl)-NADP | 100 |
| Polyethylene glycol(M4000)-$N^6$-(2-aminoethyl)-NADP | 95 |
| Polyethylene glycol(M 20000)-$N^6$-(2-aminoethyl)-NADP | 95 |
| Poly-(ethylene/maleic acid)-$N^6$-(2-aminoethyl)-NADP | 50 |
| Poly-(methylvinyl ether/maleic acid)-$N^6$-(2-aminoethyl)-NADP | 60 |
| Poly-(divinyl ether/maleic acid)-$N^6$-(2-aminoethyl)-NADP | 63 |

Note: For the $N^6$-(2-aminoethyl)NADP and $^6$-(2-aminoethyl)-NADPH derivatives $\epsilon_{267}=21000$ $M^{-1}$ $cm^{-1}$ and $\epsilon_{340}=6220$ $M^{-1}cm^{-1}$ were assumed as extinction coefficients.

G. Example 5: Preparation of CH-sepharose 4B-$N^6$-(2-aminoethyl)-NADP:

0.25 g CH-sepharose 4B (Pharmacia, with 10–14 μmol carboxyhexyl groups) steeped in 3 ml distilled water were washed over a glass frit with 25 ml distilled water. The half-dried CH-sepharose 4B was suspended in 0.45 ml distilled water and 70 mg (365 μmol) 1-(3-dimethylaminopropyl)-3-ethylcarbodiimide-HCl added. The suspension was incubated 10 min later at room temperature (pH setting to 4.8–5.0 with 0.1N NaOH or 0.1N HCl). The activated CH-sepharose 4B was washed twice within 1 minute with 10 ml distilled water and added to 0.45 ml aqueous solution with 1.4 μmol $N^6$-(2-aminoethyl)-NADP. The suspension was incubated for 16 hours at room temperature after pH setting to 4.6 (0.1N NaOH or 0.1N HCl).

After washing with 20 ml 20% LiCl and 16 ml distilled water and sedimentation in distilled water 1 ml CH-sepharose 4B-$N^6$-(2-aminoethyl)-NADP with 1 μmol bound $N^6$-(2-aminoethyl)-NADP (concentration 1 mM) were obtained with a coupling yield of 71.4%.

Preparation of Macromolecular FAD

Preparation and purification of N(1)-(2-aminoethyl)-FAD 0.5 g (0.6 mmol) FAD (Serva, di-sodium salt) were dissolved in 1 ml distilled water. To this 40 μl (0.8 mmol) ethyleneimine (Serva) was slowly added, the pH value being kept at 3.5±0.1 with 35% perchloric acid (total volume 1.5 ml). The reaction mixture was stirred for 144 hours at 30° C., pH 3.5±0.1 (set with 35% perchloric acid). The transformation of the FAD to N(1)-(2-aminoethyl)-FAD was determined by UV scanning by thin-film chromatography on silica gel (DC alu foils silica gel 60 $F_{254}$, film thickness 0.2 mm, E. Merck) with mobile phase isobutyric acid/distilled water/25% $NH_3$ in water=66/33/1 (vol./vol./vol.), pH 3.7. The reaction mixture was made up to 3 ml with distilled water. By precipitation twice and subsequent centrifuging with in each case 50 ml industrial ethanol at 4° C. the unconverted ethyleneimine soluble in the ethanol was removed.

The precipitate was dissolved in as little distilled water as possible and freeze dried. The lyophilisate was kept in a desiccator over NaOH at 4° C.

For the fractionation the freeze-dried reaction mixture with the composition 0.192 mmol FAD (32%), 0.354 mmol N(1)-(2-aminoethyl)-FAD (59%) and 0.054 mmol byproducts (9%) was dissolved in distilled water up to 20 ml. After pH setting to 5.0 with 1N HCl this solution was introduced into a cation exchanger column (60×1.5 cm, Biorex 70, 50–100 meshes, Bio-Rad) which had been brought into equilibrium against distilled water, pH 3.5. By elution at 4° C. with distilled water, pH 3.5, two fractions were successively obtained: FAD contaminated with secondary products (0.22 mmol, 46.6% in 150 ml) and secondary products (0.043 mmol, 8.9% in 100 ml) formed during the fractionation in the column. Pure N(1)-(2-aminoethyl)-FAD (0.215 mmol, 44.5%, in 1000 ml) was eluted with 0.5M LiCl, pH 3.5.

The fractions with FAD and N(1)-(2-aminoethyl)-FAD were concentrated under reduced pressure to 5 and 10 ml respectively. By precipitation 3 times and subsequent centrifuging from the N(1)-(2-aminoethyl)-FAD fraction in each case in 250 ml industrial ethanol at 4° C. LiCl was removed. The FAD fraction and N(1)-(2-aminoethyl)-FAD were freeze dried after dissolving 10 ml distilled water and stored at 4° C. in a desiccator over NaOH. The fractionation obtained is summarized in the following table:

| Compound | mmol in the reaction mixture | mmol after fractionation | % recovery | % of mmol into column |
|---|---|---|---|---|
| FAD | 0.192 | 0.192 | 100 | 32 |
| Secondary products | 0.054 | 0.171 | — | 11.8 |
| N(1)-(2-aminoethyl)-FAD | 0.354 | 0.215 | 61 | 36 |

N(1)-(2-aminoethyl)-FAD gives a positive reaction with ninhydrin (primary amino groups are present) and exhibits the maxima in the UV spectrum, usual for FAD and derivatives, at 450, 373 and 262 nm. Stimulated at 360 nm pronounced fluorescence is observed. The rf value in the aforementioned elution system for thin-film chromatography is 0.138.

B. Preparation and purification of $N^6$-(2-aminoethyl)-FAD

39 μmol N(1)-(2-aminoethyl)-FAD were dissolved in 8.3 ml distilled water and set with 0.1N LiOH to a pH value of 6.5. This solution was incubated in a water bath at 40° C. for 7 hours. A pH setting was made every hour with 0.1N LiOH. By thin-film chromatography according to A it was detected that two compounds had formed from N(1)-(2-aminoethyl)-FAD, i.e. $N^6$-(2-aminoethyl)-FAD (rf=0.177) and the presumed 1,$N^6$-ethane-adenine-FAD (rf=0.12). The composition of the incubation solution was determined by UV scanning at 265 nm by thin-film chromatography: 35% 1,$N^6$-ethaneadenine-FAD (13.5 μmol) and 65% $N^6$-(2-aminoethyl)-FAD (25.5 μmol). The incubation solution was concentrated under reduced pressure to 4 ml. After pH setting to 6.5 this solution was introduced at 4° C. into an anion exchanger column (100×0.5 cm, $AG_1X_4$, 100–200 meshes, Bio-Rad) which had been brought into equilibrium against distilled water, pH 3.5. By elution with distilled water, pH 3.5, firstly undefined decomposition products were eluted (±2 μmol, 5%). By a gradient 0–0.2M LiCl (pH 3.5, 500 ml/500 ml) successively $N^6$-(2-aminoethyl)-FAD (13.7 μmol, 53% in 400 ml) and the presumed 1,$N^6$-ethane-adenine-FAD (5.6 μmol, 40%, in 300 ml) were eluted. The two fractions were concentrated under reduced pressure to 4 ml and gel-filtered to remove the LiCl through a Sephadex G10 column (100×1 cm) which had been brought into equilibrium against distilled water.

After freeze drying the two products were stored in a desiccator over NaOH at 4° C. The fractionation obtained is summarized in the following table:

| Compound | μmol in the reaction mixture | μmol after fractionation | % recovery | % μmol into column |
| --- | --- | --- | --- | --- |
| 1,$N^6$-ethane-adenine-FAD | 13.5 | 5.5 | 40 | 14.3 |
| $N^6$-(2-aminoethyl-FAD | 25.5 | 13.7 | 53 | 35.1 |

UV spectra and first NMR data have confirmed $N^6$-(2-aminoethyl)-FAD as such. The compound gives a positive reaction with ninhydrin (primary amino group present), has $\lambda_{max}$ at 266 nm and exhibits the characteristic maxima of FAD and derivatives at 450 and 373 nm in the UV spectrum. Stimulated at 366 nm pronounced fluorescence is observed.

C. Example 1: Preparation of polyethylene gylcol-$N^6$-(2-aminoethyl)-FAD

PEG ($M_r$=20000)-$N^6$-(2-aminoethyl)-FAD:

110 mg N-hydroxysuccinimide-activated, carboxylated polyethylene glycol ($M_r$=20000, 5 μmol with 10 μmol activated carboxyl groups), made according to Bueckmann et al., Makromol. Chem. 182, 1379–1384 (1981), were dissolved in 1 ml distilled water with 5 μmol $N^6$-(2-aminoethyl)-FAD at pH 7.2, set with 0.1N NaOH, Agitation took place for 1 hour at room temperature-and pH 7.2 to 7.3 (0.1N HCl or 0.1N NaOH). The reaction mixture was gel-filtered at 4° C. through a Sephadex G 50 column (0.5×60 cm) in equilibrium against distilled water. The fraction with polyethylene glycol $N^6$-(2-aminoethyl)-FAD was concentrated to 1.7 ml with 2 μmol $N^6$-(2-aminoethyl)-FAD (concentration 1.18 mM) bound to polyethylene glycol ($M_r$=20000) with a coupling yield of 40%.

D. Example 2: Preparation of CH-sepharose 4B-$N^6$-(2-aminoethyl)-FAD:

0.25 g CH-sepharose 4B (Pharmacia, with 10–14 μmol carboxyhexyl groups) steeped in 3 ml distilled water was washed over a glass frit with 25 ml distilled water. The half-dried CH-sepharose 4B was suspended in 0.5 ml distilled water and 100 mg (520 μmol) 1-(3-dimethylaminopropyl)-3-ethyl-carbodiimide-HCl added. The suspension was incubated for 10 min at room temperature (pH setting to 4.8–5.0 with 0.1N NaOH or 0.1N HCl). The activated CH-sepharose 4B was washed within 1 minute twice with 10 ml distilled water and added to 0.5 ml aqueous solution with 2.1 μmol $N^6$-(2-aminoethyl)-FAD. The suspension was incubated for 16 hours at room temperature after pH setting to 4.6 (0.1N NaOH or 0.1N HCl).

After washing with 30 ml 20% LiCl and 20 ml distilled water and sedimentation in distilled water 1.2 ml CH-sepharose 4B-$N^6$-(2-aminoethyl)-FAD with 1.75 μmol bound $N^6$-(2-aminoethyl)-FAD (concentration 1.45 mM) were obtained with a coupling yield of 83%.

Literatur

1. Mosbach, K., Advances in Enzymology 46, 205–278 (1978)
2. Wichmann, R., Wandrey, C., Bückmann, A. F. und Kula, M.-R., Biotechn. Bioeng. 23, 2789–2802 (1981)
3. Lindberg, M., Larsson, P.-0. und Mosbach, K., Eur. J. Biochem. 40, 187–193 (1973)
4. Lowe, C. R. und Mosbach, K., Eur. J. Biochem. 49, 511–520 (1974)
5. Muramatsu, M., Urabe, I., Yamada, Y. und Okada, H., Eur. J. Biochem 80, 111–117 (1977)
6. Zappelli, P., Rossodivita, A. und Re.L., Eur. J. Biochem. 54, 475–482 (1975)
7. Zappelli, P., Pappa, R., Rossodivita, A. und Re.L., Eur. J. Biochem. 72, 309–315 (1977)
8. Schmidt, H. L. und Grenner, G., Eur. J. Blochem. 67, 295–302 (1976)
9. Weibel, M. K., Fuller, C. W., Stadel, J. M., Bückmann, A. F. Doyle, T. und Bright, H. J., Enzyme Engineering 2, 203–208 (1974)
10. Yoshikawa, M., Goto, M., Ikura, K., Sasaki, R. und Chiba, H. Agric. Biol. Chem., 46, 207–213 (1982)
11. LeGoffic F., Sicsic, S. und Vincent, C. , Eur. J. Biochem. 108, 143–148 (1980)
12. Fuller, C. W., Rubin, J.R. und Bright, H. J., Eur. J. Biochem. 103, 421–430 (1980)
13. Bückmann, A. F., Deutsches Patent 28.41.414 (1979)
14. Bückmann, A. F., Kula, M.-R., Wichmann, R. und Wandrey, C., J. Appl. Biochem. 3, 301–315 (1981)
15. Yamazaki, Y. und Maeda, H., Agric. Biol. Chem. 45, 2631–2632 (1981)
16. Zapelli, P., Pappa, R., Rossodivita, A. und Re L., Eur. J. Biochem. 89, 491–499 (1978)
17. Narasimhan, K. und Wingard, L. B., Appl. Biochem. Biotechn. 11, 221–232 (1985)

What is claimed is:

1. A process of preparing $N^6$-substituted NAD or NADP, which consists essentially of;
   (a) alkylating the NAD or NADP in the N(1)-position with ethyleneimine to obtain the corresponding N(1)-(2-aminoethyl)-NAD or N(1)-(2-aminoethyl)-NADP; and
   (b) rearranging the alkylation product to obtain the corresponding $N^6$-(2-aminoethyl)-NAD or $N^6$-(2-aminoethyl)-NADP
   said rearrangement being carried out without first reducing the alkylation product.

2. Process according to claim 1 wherein the rearrangement is carried out in an aqueous medium.

3. Process according to claim 1 wherein the rearrangement is carried out at a pH value of 4 to 9.

4. Process according to claim 1 wherein the rearrangement is carried out at a temperature of 25° to 75° C.

5. Process according to claim 3 wherein the pH value is from 5 to 8.

6. Process according to claim 5 wherein the temperature is from 40° to 60° C.

7. A process of preparing $N^6$-substituted NAD or NADP, which consists essentially of;
   (a) alkylating the NAD or NADP in the N(1)-position with ethyleneimine to obtain the corresponding N(1-(2-aminoethyl)-NAD or N(1)-(2-aminoethyl)-NADP; and
   (b) rearranging the alkylation product to obtain the corresponding $N^6$-(2-aminoethyl)-NAD or $N^6$-(2-aminoethyl)-NADP;
   said rearrangement being carried out without first reducing the alkylation product; and
   (c) covalently bonding the rearrangement product to a macromolecule.

8. A process for preparing $N^6$-substituted FAD, which consists essentially of;
(a) alkylating FAD in the N(1)-position with ethyleneimine to obtain N(1)-(2-aminoethyl)-FAD; and
(b) rearranging the alkylation product to obtain $N^6$-(2-aminoethyl)-FAD;

said rearrangemet being carried out without first reducing the alkylation product.

9. A process for preparing $N^6$-substituted FAD which consists essentially of;
(a) alkylating FAD in the N(1)-position with ethyleneimine to obtain N(1)-(2-aminoethyl)-FAD;
(b) rearranging the alkylation product to obtain $N^6$-(2-aminoethyl)-FAD;

said rearrangement being carried out without first reducing the alkylation product; and
(c) covalently bonding the alkylation product to a macromolecule.

* * * * *

UNITED STATES PATENT AND TRADEMARK OFFICE
CERTIFICATE OF CORRECTION

PATENT NO. : 5,399,681
DATED : March 21, 1995
INVENTOR(S) : Andreas F. Buckman

It is certified that error appears in the above-indentified patent and that said Letters Patent is hereby corrected as shown below:

Col. 6, line 68; "22 with 20" should read

-- 22 ml with 20 --

Col. 11; line 20; "NADP and $^6$-(2-" should read

-- NADP and $N^6$-(2- --

Signed and Sealed this

Twenty-seventh Day of June, 1995

Attest:

BRUCE LEHMAN

*Attesting Officer*   *Commissioner of Patents and Trademarks*